United States Patent [19]
Juliana et al.

[11] Patent Number: 4,873,430
[45] Date of Patent: Oct. 10, 1989

[54] METHOD AND APPARATUS FOR OPTICALLY MEASURING CHARACTERISTICS OF A THIN FILM BY DIRECTING A P-POLARIZED BEAM THROUGH AN INTEGRATING SPHERE AT THE BREWSTER'S ANGLE OF THE FILM

[75] Inventors: Anthony Juliana; Wai C. Leung, both of San Jose; Victor T. Pan, Fremont; Hal J. Rosen, Los Gatos; Timothy C. Strand, San Jose, all of Calif.

[73] Assignee: International Business Machines Corporation, Armonk, N.Y.

[21] Appl. No.: 262,558

[22] Filed: Oct. 25, 1988

[51] Int. Cl.$^4$ ............................................. G01V 5/00
[52] U.S. Cl. .................................. 250/225; 250/228; 250/560; 356/382
[58] Field of Search ...................... 250/225, 228, 560; 356/381, 382, 236, 364, 369

[56] References Cited

U.S. PATENT DOCUMENTS

| | | | |
|---|---|---|---|
| 3,985,447 | 10/1976 | Aspnes | 356/118 |
| 4,129,781 | 12/1978 | Doyle | 250/341 |
| 4,626,101 | 12/1986 | Ogawa et al. | 356/237 |
| 4,707,611 | 11/1987 | Southwell | 250/560 |
| 4,745,291 | 5/1988 | Niiya | 356/382 |

OTHER PUBLICATIONS

M. L. E. Chwalow et al., "Automatic Brewster's Angle Thin Film Thickness Measurement Spectrophotometer", IBM Technical Disclosure Bulletin, vol. 20, No. 8, Jan. 1978, pp. 3313-3314.

Primary Examiner—David C. Nelms
Assistant Examiner—William L. Oen
Attorney, Agent, or Firm—Henry E. Otto, Jr.

[57] ABSTRACT

A method for optically measuring at least one characteristic of a thin film on a reflecting substrate. A p-polarized beam of collimated light of known intensity is directed through an integrating sphere onto the film at substantially the Brewster's angle of the film. All the light is reflected into the sphere, including all diffusely reflected light as well as the light specularly reflected at a region inside the sphere where the specularly reflected light is incident. A reflective surface is provided for determining the thickness of the film as a function of the total intensity of light sensed within the sphere. An absorptive surface is provided at said region for absorbing the specularly reflected light for determining the porosity or surface roughness of the film based on the intensity of the diffused light sensed within the sphere not reflected from the substrate.

15 Claims, 1 Drawing Sheet

METHOD AND APPARATUS FOR OPTICALLY MEASURING CHARACTERISTICS OF A THIN FILM BY DIRECTING A P-POLARIZED BEAM THROUGH AN INTEGRATING SPHERE AT THE BREWSTER'S ANGLE OF THE FILM

FIELD OF THE INVENTION

This invention relates to a method and apparatus for optically measuring characteristics of a thin, light transmitting film on a reflecting substrate, and more particularly to a method and apparatus for measuring thickness, porosity or surface roughness of a thin film.

BACKGROUND OF THE INVENTION

Various techniques have heretofore been used to measure the thickness of a thin, light transmitting film on a reflecting substrate. Usually they involve measuring the intensity of the polarized light transmitted through or reflected from the film at an angle. These ellipsometric techniques and other methods based upon optical interferometry and also X-ray fluorescence techniques tend to be unduly time consuming. X-ray fluorescence techniques are also incapable of measuring very thin inhomogeneous films or coatings having thicknesses as low as 50 nanometers. Moreover, most are incapable of mapping variations in the thickness of the film over its entire surface due to limitations in speed and/or lateral resolution.

Porosity of a thin film or coating has heretofore been obtained using density measurements and gas adsorption. These techniques provide only an overall picture of porosity. They are not appropriate for measuring local variations in porosity over the entire area of the film or coating and are too time consuming for on-line inspection.

The most pertinent prior art of which applicants are aware is U.S. Pat. No. 4,129,781, which discloses an arrangement for measuring the thickness of a thin film using collimated light impinging at Brewster's angle. However, this patented arrangement will not provide satisfactory measurements on inhomogeneous thin films or coatings which isotropically scatter light. It claims to satisfactorily measure thickness of a film or coating on a striated substrate using absorption measurements; but even using such grooved substrates, the accuracy of the measurement is limited because there will always be some light scattering, and light scattering is not taken into account.

U.S. Pat. No. 3,985,447 discloses another method for measuring the thickness of a thin film using polarized light which impinges on the film at the Brewster's angle of the film. This and other ellipsometric methods examine the phase differences between s and p polarizations and rely on interference effect; however, these techniques can provide spurious results in the presence of diffused or scattered light.

The IBM Technical Disclosure Bulletin dated January, 1978, at p. 3133, discloses an instrument capable of measuring individual layer thicknesses of a composite film by measuring the relative intensity of the s and p components of polarized light reflected at Brewster's angle, as the wavelength of the incident light is varied.

None of these arrangements involving impinging light at the Brewster's angle of the film employ an integrating sphere; and all are capable only of measuring the thickness of the film.

U.S. Pat. No. 4,626,101 discloses a laser beam directed either vertically or at a slight angle off vertical into an integrating sphere that has an opening in its lower portion to permit light to be reflected back into the sphere from a specimen to be examined. The intensity of the scattered light collected on the reflective surface within the sphere is detected, converted from an analog to a digital value, and compared with a reference value to classify the digital data on the basis of the size of a surface defect. An R-$\theta$ turntable is provided to enable sampling the entire surface of the specimen. However, this arrangement does not disclose or suggest having the laser beam impinge at the Brewster's angle of the specimen to minimize interference effects and thus can not measure coating thickness.

There is a need for an improved method and apparatus which permits on-line inspection of a thin film by optically measuring various characteristics, such as the thickness, porosity and surface roughness of the film.

SUMMARY OF THE INVENTION

Toward this end, and according to the invention, a p-polarized beam of collimated light of known intensity is directed through apertures in an integrating sphere onto a thin film at substantially the Brewster's angle of the film. The thin film is closely adjacent the sphere and is supported on a reflecting substrate. As a result, all diffusely reflected light, as well as the light which is specularly reflected at a region inside the sphere where the specularly reflected is incident, is reflected into the sphere. When a reflective surface is provided at said region, the thickness of the film is determined as a function of the total intensity of light sensed; whereas when an absorptive surface is provided at said region, the specularly reflected light is absorbed and a characteristic of the film, such as its porosity or surface roughness, is determined based on the intensity of the diffused light not reflected from the substrate. Means, such as an R-$\theta$ stage, is employed for moving the substrate relative to the sphere for mapping such characteristics over selectable areas of the film or the entire film.

DESCRIPTION OF PREFERRED EMBODIMENT

As hereinafter used, the term "thin film" or "film" connotes a thin film or coating through which at least some light is transmissible.

Figure 1:
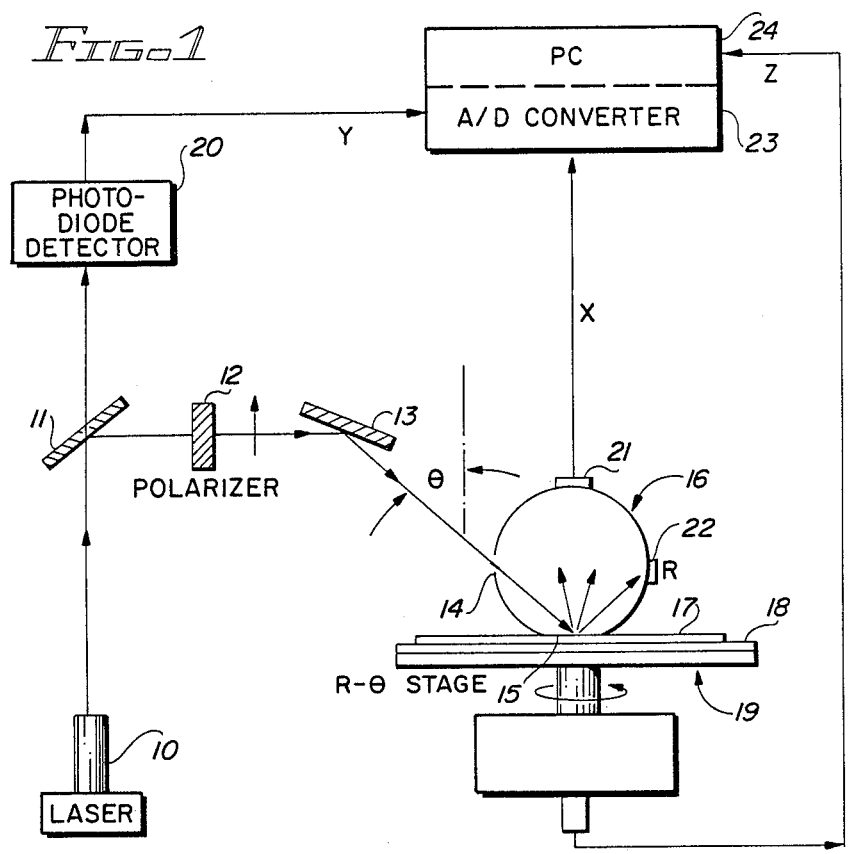
FIG. 1 is a schematic diagram of an apparatus embodying the invention for optically measuring various characteristics of a thin film.

As illustrated in FIG. 1, the apparatus embodying the invention comprises a an appropriate light source laser 10, preferably a He-Ne laser, for directing a polarized beam of collimated light at a beam splitter 11. Beam splitter 11 redirects a portion of the beam through a p-polarizing lens 12 to a mirror 13. Mirror 13 redirects the p-polarized beam through ports 14, 15 in an integrating sphere 16 having a reflective coating on its hollow interior surface. Port 15 closely is adjacent a thin film 17, the characteristics of which are to be measured. Film 17 is disposed on a reflecting substrate 18 that is mounted for rotation and radial stepping on a conventional R-$\theta$ stage 19. Beam splitter 11 passes the remaining portion of the laser beam to a photo diode detector 20.

Figure 2:
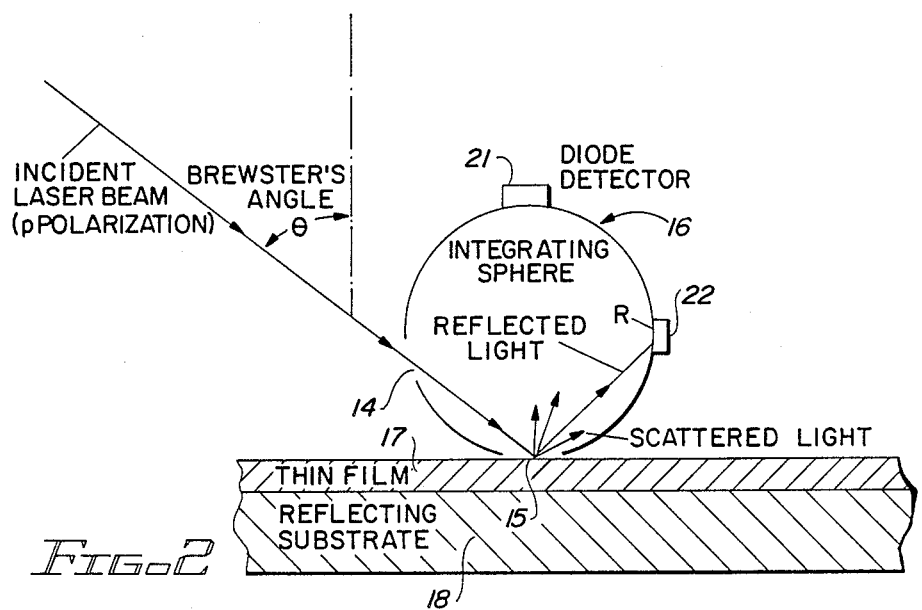
FIG. 2 is a view, to an enlarged scale, of a portion of the apparatus shown in FIG. 1.

According to the invention, and as best shown in FIG. 2, the p-polarized beam of collimated light passes through ports 14, 15 and impinges on film 17 at the Brewster's angle $\theta$ of the film. Use of p-polarized collimated light eliminates reflection which would otherwise occur at the entry or up-beam side of the film 17. All the light is reflected from film 17 into the interior of the sphere. The light is specularly reflected to a region R in the wall of the sphere 16 where the specularly reflected light is incident. A photodiode detector 21 is mounted in the wall of sphere 16 to sense the light intensity within the sphere.

According to a feature of the invention, a cap or wafer 22 or the like is removably mounted in the wall of sphere 16 at region R. Wafer 22 preferably has a reflective surface on one side and an absorptive surface on the opposite side. When inserted with the reflective surface of wafer 22 facing the sphere interior, all light including all diffusely reflected light and the specularly reflected light will be sensed by detector 21. The output X of detector 21 is supplied to an analog-to-digital converter 23. The digitized output indicative of light intensity is used by a microprocessor 24 to compute the thickness of the film at a specific minute area thereon. A digital output Z from the R-$\theta$ stage 19 is also supplied to the microprocessor 24 to identify the radial and rotary position at which the thickness was measured.

The R-$\theta$ stage 19, in conventional manner, steps the substrate 18 to a plurality of discrete rotary positions, at each of which a different area of the film is sequentially exposed to the p-polarized laser beam through ports 14, 15; and upon completion of each revolution, the stage increments radially to expose discrete areas or segments in a different annular portion of the film to the laser beam. As a result, a series of digital outputs are generated identifying the radial/rotary positions at which the various measurements are sequentially taken for enabling a map to be created denoting variations in surface thickness over the entire surface of the film.

When wafer 22 is mounted at region R with its absorptive surface facing the sphere interior, the specularly reflected light is totally absorbed. Detector 21 will thus sense only the diffusely reflected light. The output from detector 21 is supplied via A/D convertor 23 to microprocessor 24 and used to compute the porosity or surface roughness of film 17. This is possible because if a film is porous, each pore acts as a scattering center. The more scattering centers in the film, the more total scattered energy will be measured, at least in the spectral regions where the film is not highly absorbing. From an optical standpoint, pores in a homogeneous medium represent a discontinuity in the index of refraction. The R-$\theta$ stage 19 will increment the film rotationally and radially, as earlier explained, to enable porosity variations to be mapped over the entire surface of the film.

It will be understood that, with the absorptive surface of wafer 22 facing inward, the diffusely reflected light can also be used to measure surface roughness, or stated differently, variations in surface smoothness due to scratches, dust, defects or other causes.

To provide a basis for comparison, the measurement made at each discrete radial-rotary position preferably is compared to the average scattering intensity of the diffusely reflected light over the entire surface of film 17 or to a preselected standard.

According to a feature of the invention, the digitized output X preferably is divided by the digitized output Y of photodiode detector 20 to compensate for any variations in intensity of the laser beam.

The apparatus used to digitally encode the radial-rotary position at which each measurement is being made, to compare the digitized output of diode 21 with a standard, to control the microprocessor 24, and to interpret, store and/or display the measurements forms no part of the present invention; and it may, if desired, be similar to that shown and described in the above-cited U.S. Pat. No. 4,626,101.

If desired, laser 10 may be replaced by any other source of collimated light, such as a tungsten lamp; in such case, however, the output from such source may require polarization. Also, depending upon the configuration of the apparatus, the p-polarizing lens 12 may or may not be necessary.

It should also be noted that light-transmitting films may be disposed between the reflective substrate and the particular thin film or coating to be measured. In the case of multiple transmitting layers, the characteristics of each layer can be measured by selecting a wavelength at which that layer is significantly absorptive and the other layers are significantly transparent. Use of p-polarized collimated light eliminates reflections at the boundaries between layers.

The foregoing and other variations may be made in the method and apparatus herein described. They are therefore considered to be merely illustrative and the invention is not to be considered limited except as specified in the claims.

We claim:

1. A method of optically measuring at least one characteristic of a thin film on a reflecting substrate, comprising the steps of:
    directing a p-polarized beam of collimated light of known intensity through one aperture in an integrating sphere and via a second aperture therein onto the film at substantially the Brewster's angle of the film;
    reflecting all the light into the sphere, including (i) all diffusely reflected light and (ii) the light specularly reflected at a region inside the sphere where the specularly reflected light is incident; and
    sensing the light intensity within the sphere for measuring said at least one characteristic of the film.

2. The method of claim 1, including the step of
    providing at said region a reflective surface for determining the thickness of the film as a function of the total intensity of light sensed.

3. The method of claim 1, including the step of:
    providing at said region an absorptive surface for absorbing the specularly reflected light for determining at least one characteristic of the film based on the intensity of the diffused light not reflected from the substrate.

4. The method of claim 3, wherein the characteristic is porosity.

5. The method of claim 3, wherein the characteristic is surface roughness.

6. The method of claim 1, including the step of:
    moving the substrate relative to the sphere for mapping selectable areas of the film.

7. The method of claim 6, wherein an R-$\theta$ stage is employed for the moving step.

8. A method of optically measuring at least one characteristic of a thin film on a reflecting substrate, comprising the steps of:
    splitting a beam of collimated light from a source;

passing one portion of the beam through a photodiode detector to generate one analog signal corresponding to the light intensity of the source;

p-polarizing the other portion of the beam and directing it into an integrating sphere and onto the film at substantially the Brewster's angle of the film;

reflecting all the light into the sphere, including (i) all diffusely reflected light and (ii) the light specularly reflected at a region inside the sphere where the specularly reflected light is incident;

generating another analog signal corresponding to the sensed light intensity within the sphere;

converting both analog signals to digital signals and dividing the digitized signals of said one and other signals to compensate for variations in light intensity from the source; and using said other digitized signal measuring a characteristic of the film.

9. The method of claim 8, including the further step of:

moving the substrate relative to the sphere; and generating digital signals indicative of the location on the film at which the characteristic is being measured for providing said other digitized signals for each such location to map the characteristic at multiple locations.

10. Apparatus for optically measuring at least one characteristic of a thin film on a reflecting substrate, comprising:

an integrating sphere;

means for directing a p-polarized beam of collimated light of known intensity through the sphere and onto the film at substantially the Brewster's angle of the film;

means for maintaining the film substantially in contact with the sphere so that all of the light will be reflected into the sphere, including (i) all diffusely reflected light and (ii) the light specularly reflected at a region inside the sphere where the specularly reflected light is incident;

light-sensitive detecting means for generating an analog signal indicative of the intensity of light within the sphere; and means, including an analog-to-digital converter and processor, for measuring said at least one characteristic of the film from said analog signal.

11. The apparatus of claim 10, including means at said region for reflecting the specularly reflected light for enabling the last-mentioned means to determine the thickness of the film as a function of the total light intensity sensed by said detecting means.

12. The apparatus of claim 10, including means at said region for absorbing the specularly reflected light for enabling the last-mentioned means to determine a characteristic of the film based solely on the intensity of the diffused light not reflected from the substrate.

13. The apparatus of claim 12, wherein the characteristic is porosity.

14. The apparatus of claim 12 wherein the characteristic is surface roughness.

15. An apparatus for optically measuring at least one characteristic of a thin film on a reflecting substrate, comprising:

means for splitting a beam of collimated light from a source;

detector means through which one portion of the beam is passed to generate one analog signal corresponding to the light intensity of the source;

an integrating sphere closely adjacent the film;

means for p-polarizing the other portion of the beam and directing it into the sphere and onto the film at substantially the Brewster's angle of the film for causing all the light to be reflected into the sphere, including (i) all diffusely reflected light and (ii) the light specularly reflected at a region inside the sphere where the specularly reflected light is incident;

means for generating another analog signal corresponding to the sensed light intensity within the sphere;

means for converting both analog signals to digital signals and dividing the digitized signals of said one and other signals to compensate for variations in light intensity from the source; and mean responsive to said other digitized signal for measuring a characteristic of the film.

* * * * *